(12) United States Patent
Prevost et al.

(10) Patent No.: US 7,034,024 B1
(45) Date of Patent: Apr. 25, 2006

(54) PRODUCT INHIBITING TRANSDUCTION OF G HETEROTRIMERIC PROTEIN SIGNALS COMBINED WITH ANOTHER ANTI-CANCER AGENT FOR THERAPEUTIC USE IN CANCER TREATMENT

(75) Inventors: Grégoire Prevost, Antony (FR); Marie-Odile Lonchampt, Chevilly-Larue (FR); Thomas Gordon, Medway, MA (US); Barry Morgan, Franklin, MA (US)

(73) Assignee: Societe de Conseils de Recherches et d'Applications Scientifiques (S.C.R.A.S.), (FR)

( * ) Notice: Subject to any disclaimer, the term of this patent is extended or adjusted under 35 U.S.C. 154(b) by 0 days.

(21) Appl. No.: 10/129,569

(22) PCT Filed: Nov. 8, 2000

(86) PCT No.: PCT/FR00/03098

§ 371 (c)(1),
(2), (4) Date: Jun. 21, 2002

(87) PCT Pub. No.: WO01/34203

PCT Pub. Date: May 17, 2001

(30) Foreign Application Priority Data

Nov. 9, 1999 (FR) .................................. 99 14037
Jan. 6, 2000 (FR) .................................. 00 00104

(51) Int. Cl.
*A61K 31/495* (2006.01)
(52) U.S. Cl. ..................................... 514/249; 514/283
(58) Field of Classification Search ................ 514/283, 514/649, 263.4, 80, 280, 410, 449, 290, 359, 514/249; 544/350
See application file for complete search history.

(56) References Cited

U.S. PATENT DOCUMENTS

| 5,565,478 A | * | 10/1996 | Kohn et al. | .................. | 514/359 |
| 6,333,333 B1 | * | 12/2001 | Bishop et al. | .............. | 514/290 |
| 6,342,487 B1 | * | 1/2002 | Riou et al. | .................... | 514/80 |
| 6,617,331 B1 | * | 9/2003 | Gray et al. | .............. | 514/263.4 |

FOREIGN PATENT DOCUMENTS

WO 9730053 8/1997

* cited by examiner

*Primary Examiner*—Michael Hartley
(74) *Attorney, Agent, or Firm*—Charles A. Muserlian

(57) ABSTRACT

The invention concerns a product inhibiting transduction of G heterotrimeric protein signals combined with another anti-cancer agent, in particular farnesyltransferase inhibitors, taxol or gemcitabin, for simultaneous, separate or prolonged therapeutic use in cancer treatment.

2 Claims, No Drawings

PRODUCT INHIBITING TRANSDUCTION OF G HETEROTRIMERIC PROTEIN SIGNALS COMBINED WITH ANOTHER ANTI-CANCER AGENT FOR THERAPEUTIC USE IN CANCER TREATMENT

This application is a 371 of PCT/FR00/03098 filed Nov. 8, 2000.

The present invention relates to a product comprising at least one transduction inhibitor of heterotrimeric G protein signals, that preferably corresponds to general formula (I) defined below, combined with at least one other anti-cancer agent, preferably chosen from the group comprising taxol, taxol analogues, gemcitabine and prenyltransferase inhibitors, particularly the compounds of general formulae (II) or (III) defined below, for therapeutic use, simultaneously, separately or spread over a period of time, in the treatment of cancer.

The development of new anti-cancer treatments occurs largely by the discovery of effective combinations between different therapeutic classes to accentuate the antitumorous effect of each class.

The combination of the anti-Her-2/neu antibody and cisplatin or etoposide inhibits the proliferation of mammary tumor cells in a more significant manner than the simple addition of the effects of each product (cf. Pegram, M., et al., *Oncogene*, 18 (1999): 2241–2251). The combination of this antibody with taxol or methotrexate shows an addition of the effects whilst its combination with 5-fluorouracyl shows an antagonism of the products (McGuire W. P. et al., *Semin. Oncol.* 1997 Feb. 24 (1 Suppl 2):S2-13–S2-16).

The farnesyltransferase inhibitors act in synergy with agents which depolymerise microtubules (taxol, epothilones) (cf. Moasser et al., *Proc. Natl. Acad. Sci. U.S.A.* (1998), 95, 1369–1374). The combination of farnesyltransferase inhibitors with cytotoxic doxorubicin, cisplatin or 5-fluorouracyl shows only an addition of the effects.

The heterotrimeric G proteins are, in fact, the structural association of three distinct sub-units called $\alpha$, $\beta$ and $\gamma$, but function as dissociable entities constituted by sub-units $\alpha$ on the one hand and $\beta/\gamma$ dimers on the other. Different forms of sub-units of $\alpha$, $\beta$, and $\gamma$ type are described.

The G proteins participate in the transmission of signals outside the cell, thanks to its interaction with receptors with seven transmembrane domains, inside using different effectors including adenylate cyclase, phospholipase C or also the ionic channels. The adenylate cyclase enzyme generates cyclic adenosine monophosphate (cAMP) (cf. Gilman, *Biosci. Rep.* (1995), 15, 65–97). Thus it is known, that in order to activate adenylate cyclase, it is necessary form the G proteins to be transitionally in a heterotrimeric form, in which form the monomer constituted by an $\alpha$ sub-unit is associated with the dimer constituted by the $\beta$ and $\gamma$ sub-units. It is also known that for the G proteins to be found in their heterotrimeric form, they must be fixed by their $\gamma$ sub-units to the membrane. It is only in this situation that the signal outside the cell can activate the $\alpha$ sub-unit of a G protein, which can, after disassociation, modulate the effectors such as adenylate cyclase and modulate the production of cAMP.

It is also known that the $\beta/\gamma$ dimers can directly activate the effectors leading to the activation of kinases regulated by extracellular signals (ERKS) or MAP kinases. A direct link between the $\beta/\gamma$ sub-units and the src or src-like kinases has been demonstrated (cf. Gutkind, *J. Biol. Chem.* (1998), 273, 1839–1842).

The harmful effects of an abnormal cAMP level are also known and occur in particular at the level of the following biological functions or disorders: smell, taste, light perception, neurotransmission, neurodegeneration, endocrine and exocrine gland functions, autocrine and paracrine regulation, arterial tension, embryogenesis, benign cell proliferation, oncogenesis, viral infection and immunological functions, diabetes and obesity.

The Applicant has itself already described in PCT Patent Application WO 00/02881 the use of the compounds of general formula (I) as defined hereafter as G protein inhibitors. Certain products had been described previously in the PCT Patent Application WO 97/30053.

Prenyltransferase inhibitors are already used in the field of cancer treatment (cf. Sebti et al., *Pharmacol. Ther.* (1997), 74, 103–114; Sepp-Lorenzino et al., *Cancer Res.* (1997), 55, 5302–5309). The usefulness of prenyltransferase inhibitors in this type of treatment comes from their action which prevents prenylation at the level of the Ras substrate. However, the prenylation of certain forms of Ras is not modified by the prenylation inhibitors (Lerner et al., *Oncogene* (1997), 15, 1283–1288).

As far as the anti-cancer agents are concerned, prenyltransferase inhibitors are in particular described in the following Patent Applications: PCT Applications WO 97/21701, WO 97/16443, WO 98/00409, WO 96/21456, WO 97/24378, WO 97/17321, WO 97/18813, WO 95/00497; U.S. Pat. No. 5,532,359, U.S. Pat. No. 5,523,430, U.S. Pat. No. 5,510,510 and U.S. Pat. No. 5,627,202. Moreover, the compounds of general formula (II) have been described in PCT Patent Application WO 00/39130. Taxol is in particular described in *Merck Index*, 11th ed., 1989, under heading number 9049 and in the references cited. Camptothecin analogues have in particular been described in the U.S. Pat. No. 4,894,456 and in the PCT Patent Applications WO 94/11376, WO 97/00876, WO 98/28304, WO 98/28305, WO 99/11646 and WO 99/33829.

A product according to the invention offers the advantage of being able to use lower doses of the anti-cancer agents chosen, which has the main effect of reducing the toxicity of the treatment whilst obtaining a pharmacological effect with a minimum of additive.

A subject of the invention is therefore a product comprising at least one transduction inhibitor of heterotrimeric G protein signals combined with at least one anti-cancer agent, preferably chosen from the group comprising taxol, taxol analogues, gemcitabine and prenyltransferase inhibitors, for therapeutic use simultaneously, separately or spread over a period of time, in the treatment of cancer.

Preferably, the prenyltransferase inhibitor combined with the transduction inhibitor of heterotrimeric G protein signals is a farnesyltransferase inhibitor.

Although taxol, taxol analogues, gemcitabine and prenyltransferase inhibitors are preferred, a number of other anti-cancer agents can be also combined, according to the invention, with a transduction inhibitor of heterotrimeric G protein signals, for example: enzyme inhibitors such as topoisomerase inhibitors such as camptothecin and camptothecin analogues (in the form of analogues comprising an E lactonic ring with six members such as for example the compounds described in PCT Patent Application WO 94/11376, in the form of analogues comprising an E lactonic ring with seven members such as for example the compounds described in PCT Patent Application WO 97/00876 or also in the form of open tetracyclic analogues such as for example the compounds described in the PCT Patent Application WO 99/33829), Cdc25 phosphatase inhibitors, MAP kinase or MAP kinase kinase inhibitors, protein kinase C inhibitors, tyrosine kinase inhibitors, telomerase inhibitors; inductors of apoptosis; alkylating agents such as cisplatin; anti-metabolic agents such as 5-fluorouracil; differentiation agents; cell spindle poisons; angiogenesis inhibitors; anti-hormones or antagonists of the steroid receptors; antioxidants; antisense agents; anti-p53 agents (gene therapy); chemo-prevention agents; anti-viral agents; immuno-therapeutic agents; antibodies such as heregulin.

Preferably, the transduction inhibitor of heterotrimeric G protein signals is a compound of general formula (I)

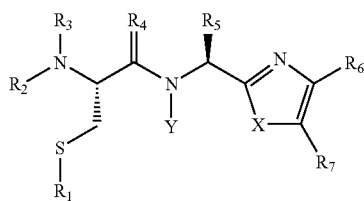

(I)

corresponding to sub-formulae ($I_A$) or ($I_B$):

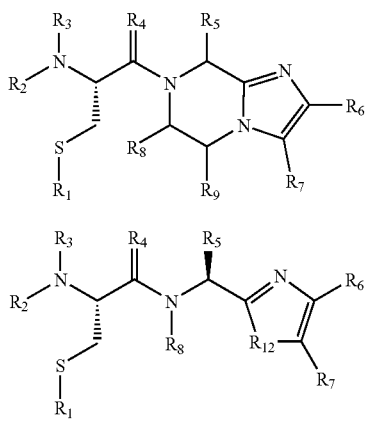

in which:

X represents $R_{12}$ and Y represents $R_8$, or X and Y complete a ring with 6 members, the X—Y mixture representing the —CH($R_8$)—CH($R_9$)— radical;

$R_1$ represents H, an alkyl or alkylthio radical;

$R_2$ and $R_3$ independently represent H or an alkyl radical;

$R_4$ represents $H_2$ or O;

$R_5$ represents H, or one of the alkyl, alkenyl, alkynyl, aryl, aralkyl, heterocyclyl or heterocyclylalkyl radicals, these radicals being able to be optionally substituted by radicals chosen from the group comprising an alkyl radical, —O—$R_{10}$, —S(O)$_m$$R_{10}$ (m representing 0, 1, or 2), —N($R_{10}$)($R_{11}$), —N—C(O)—$R_{10}$, —NH—(SO$_2$)—$R_{10}$, —CO$_2$—$R_{10}$, C(O)—N($R_{10}$)($R_{11}$), and —(SO$_2$)—N($R_{10}$)($R_{11}$);

$R_6$ and $R_7$ independently represent H, a —C(O)—NH—CHR$_{13}$—CO$_2$$R_{14}$ radical, or one of the alkyl, aryl, aralkyl, heterocyclyl or heterocyclylalkyl radicals, these radicals being optionally substituted by radicals chosen from the group comprising OH, alkyl or alkoxy, N($R_{10}$)($R_{11}$), COOH, CON($R_{10}$)($R_{11}$), and halo radicals, or $R_6$ and $R_7$ together form an aryl radical or a heterocycle;

$R_8$ and $R_9$ independently represent H or one of the alkyl, aryl, aralkyl, heterocyclyl or heterocyclylalkyl radicals, these radicals being able to be optionally substituted by radicals chosen from the group comprising OH, alkyl or alkoxy, N($R_{10}$)($R_{11}$), COOH, CON($R_{10}$)($R_{11}$) and halo radicals, or $R_8$ and $R_9$ together form an aryl radical or a heterocycle;

$R_{10}$ and $R_{11}$, independently represent H, an aryl or heterocyclyl, or an alkyl, aralkyl or heterocyclylalkyl radical;

$R_{12}$ represents N$R_9$, S, or O;

$R_{13}$ represents an alkyl radical optionally substituted by a radical chosen from the alkyl, —O$R_{10}$, —S(O)$_m$$R_{10}$ (m representing 0, 1, or 2) and —N($R_{10}$)($R_{11}$) radicals;

$R_{14}$ represents H or an alkyl radical;

or a pharmaceutically acceptable salt of such a compound.

By lower alkyl radical, is meant a linear or branched alkyl radical containing 1 to 6 carbon atoms, and in particular the methyl, ethyl, propyl, isopropyl, butyl, isobutyl, sec-butyl and tert-butyl, pentyl, neopentyl, isopentyl, hexyl, isohexyl radicals. By heterocycle radical, is meant a radical constituted by one or more rings and including at least one heteroatom. By lower arylalkyl, heterocycle alkyl, alkylthio or alkoxy radical, is meant the radicals of which the alkyl radical has the meaning as indicated previously.

Preferably, the compounds of general formula (I) are such that:

X and Y complete a ring with 6 members, the X—Y combination representing the —CH($R_8$)—CH($R_9$)— radical;

$R_1$ represents an alkyl radical or lower;

$R_2$ and $R_3$ represent H;

$R_4$ represents O;

$R_5$ represents H, or one of the lower alkyl, cycloalkyl, cycloalkylalkyl, lower arylsulphonylalkyl, lower aralkoxyalkyl radicals, these radicals being able to be optionally substituted by radicals chosen from the group comprising a lower alkyl or —O—$R_{10}$ radical;

$R_6$ and $R_7$ independently represent H or an aryl radical optionally substituted by radicals chosen from the group comprising the OH, alkyl or lower alkoxy radicals, $R_8$ and $R_9$ represent H;

and $R_{10}$ and $R_{11}$, independently represent H or a lower alkyl radical.

The following compounds of general formula (I) are in particular preferred for the invention:

7-(2-amino-1-oxo-3-thiopropyl)-8-(cyclohexylmethyl)-2-(2-methylphenyl)-5,6,7,8-tetrahydroimidazo[1,2a]pyrazine;

7-(2-amino-1-oxo-3-thiopropyl)-8-butyl-2-(2-methoxyphenyl)-5,6,7,8-tetrahydroimidazo[1,2a]pyrazine;

bis-1,1'-[7-(2-amino-1-oxo-3-thiopropyl)-2-(2-methoxyphenyl)-8-(1-methylpropyl)-5,6,7,8-tetrahydroimidazo[1,2a]pyrazine]disulphide;

bis-1,1'-[7-(2-amino-1-oxo-3-thiopropyl)-8-(cyclohexylmethyl)-2-(2-methoxyphenyl)-5,6,7,8-tetrahydroimidazo[1,2a]pyrazine disulphide;

bis-1,1'-7-(2-amino-1-oxo-3-thiopropyl-(2-(1-naphthyl)-8-(2-methylpropyl)-5,6,7,8-tetrahydroimidazo[1,2a]pyrazin-7-yl)disulphide;

7-(2-amino-1-oxo-3-thiopropyl)-8-(cyclohexylmethyl)-2-phenyl-5,6,7,8-tetrahydroimidazo[1,2a]pyrazine;

7-(2-amino-1-oxo-3-thiopropyl)-2-(2-methoxyphenyl)-8-(phenylmethoxy)methyl-5,6,7,8-tetrahydroimidazo[1,2a]pyrazine;

7-(2-amino-1-oxo-3-thiopropyl)-2-(2-methoxyphenyl)-8-(1-phenylmethoxy)ethyl-5,6,7,8-tetrahydroimidazo[1,2a]pyrazine;

7-(2-amino-1-oxo-3-thiopropyl)-2-(2-methoxyphenyl)-8-(phenoxyethyl)-5,6,7,8-tetrahydroimidazo[1,2a]pyrazine;

7-(2-amino-1-oxo-3-thiopropyl)-2-(2-methoxyphenyl)-8-(phenoxyethyl)-5,6,7,8-tetrahydro-imidazo[1,2a]pyrazine, or its dimeric form;

and 7-(2-amino-1-oxo-3-thiopropyl)-2-(2-methoxyphenyl)-8-(phenylsulphonylethyl) -5,6,7,8-tetrahydro-imidazo[1,2a]pyrazine;

or a pharmaceutically acceptable salt of one of the latter.

Preferably, when the anti-cancer agent combined with a transduction inhibitor of heterotrimeric G protein signals is a prenyltransferase inhibitor, it is a farnesyltransferase inhibitor.

More preferentially, the farnesyltransferase inhibitor is chosen from the group composed:

of a compound of general formula (II)

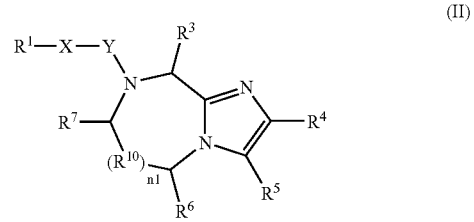

(II)

in which:

n1 represents 0 or 1;

X represents, independently, each time that it occurs, $(CHR^{11})_{n3}(CH_2)_{n4}Z(CH_2)_{n5}$;

Z representing O, $N(R^{12})$, S, or a bond;

n3 representing, independently, each time that it occurs, 0 or 1;

each of n4 and n5 representing, independently, each time that they occur, 0, 1, 2, or 3;

Y represents, independently, each time that it occurs, CO, $CH_2$, CS, or a bond;

$R^1$ represents one of the

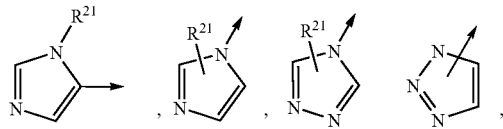

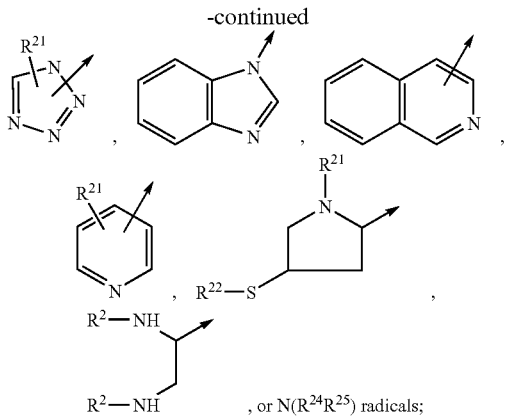

, or $N(R^{24}R^{25})$ radicals;

each of $R^2$, $R^{11}$, and $R^{12}$ representing, independently, each time that it occurs, H or an optionally substituted radical chosen from the group consisting of a $(C_{1-6})$alkyl radical and an aryl radical, said optionally substituted radical being optionally substituted by at least one radical chosen from the $R^8$ and $R^{30}$ radicals, each substituent being chosen independently of the others;

$R^3$ represents, independently, each time that it occurs, H or an optionally substituted radical chosen from the group consisting of the $(C_{1-6})$alkyl, $(C_{2-6})$alkenyl, $(C_{2-6})$alkynyl, $(C_{3-6})$cycloalkyl, $(C_{3-6})$cycloalkyl$(C_{1-6})$alkyl, $(C_{5-7})$cycloalkenyl, $(C_{5-7})$cycloalkenyl$(C_{1-6})$alkyl, aryl, aryl$(C_{1-6})$alkyl, heterocyclyl, and heterocyclyl$(C_{1-6})$alkyl radicals, said optionally substituted radical being optionally substituted by at least one radical chosen from the $R^{30}$ radicals, each substituent being chosen independently of the others;

each of $R^4$ and $R^5$ represents, independently, each time that it occurs, H or an optionally substituted radical chosen from the group consisting of the $(C_{1-6})$alkyl, $(C_{3-6})$cycloalkyl, aryl and heterocyclyl radicals, said optionally substituted radical being optionally substituted by at least one radical chosen from the $R^{30}$ radicals, each substituent being chosen independently of the others, or $R^4$ and $R^5$ taken together with the carbon atoms to which they are attached together form an aryl radical;

$R^6$ represents, independently, each time that it occurs, H or an optionally substituted radical chosen from the group consisting of the $(C_{1-6})$alkyl, $(C_{2-6})$alkenyl, $(C_{3-6})$cycloalkyl, $(C_{3-6})$cycloalkyl$(C_{1-6})$alkyl, $(C_{5-7})$cycloalkenyl, $(C_{5-7})$cycloalkenyl$(C_{1-6})$alkyl, aryl, aryl$(C_{1-6})$alkyl, heterocyclyl and heterocyclyl$(C_{1-6})$alkyl radicals, said optionally substituted radical being optionally substituted by at least one radical chosen from the OH, $(C_{1-6})$alkyl, $(C_{1-6})$alkoxy, $-N(R^8R^9)$, $-COOH$, $-CON(R^8R^9)$ and halo radicals, each substituent being chosen independently of the others;

Each time that it occurs, $R^7$ represents, independently, H, $=O$, $=S$, H or an optionally substituted radical chosen from the group consisting of the $(C_{1-6})$alkyl, $(C_{2-6})$alkenyl, $(C_{3-6})$cycloalkyl, $(C_{3-6})$cycloalkyl$(C_{1-6})$alkyl, $(C_{5-7})$cycloalkenyl, $(C_{5-7})$cycloalkenyl$(C_{1-6})$alkyl, aryl, aryl$(C_{1-6})$alkyl, heterocyclyl and heterocyclyl$(C_{1-6})$alkyl radicals, said optionally substituted radical being optionally substituted by at least one radical chosen from the OH, $(C_{1-6})$alkyl, $(C_{1-6})$alkoxy, $-N(R^8R^9)$, $-COOH$, $-CON(R^8R^9)$ and halo radicals, each substituent being chosen independently of the others;

each of $R^8$ and $R^9$ representing, independently, each time that it occurs, H, $(C_{1-6})$alkyl, $(C_{2-6})$alkenyl, $(C_{2-6})$alkynyl, aryl, or aryl$(C_{1-6})$alkyl;

$R^{10}$ represents C;

or, when n1=0, $R^6$ and $R^7$ can be taken together with the carbon atoms to which they are attached to form an aryl or cyclohexyl radical;

$R^{21}$ represents, independently, each time that it occurs, H or an optionally substituted radical chosen from the group consisting of the $(C_{1-6})$alkyl and aryl$(C_{1-6})$alkyl radicals, said optionally substituted radical being optionally substituted by at least one radical chosen from the $R^8$ and $R^{30}$ radicals, each substituent being chosen independently of the others;

$R^{22}$ represents H, $(C_{1-6})$alkylthio, $(C_{3-6})$cycloalkylthio, $R^8$—CO—, or a substituent of formula

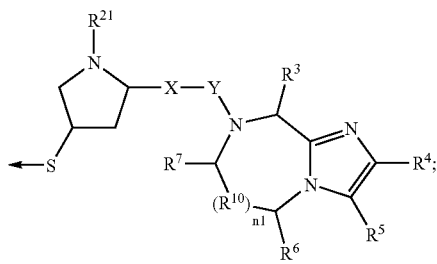

each of $R^{24}$ and $R^{25}$ represents, independently, each time that it occurs, H, $(C_{1-6})$alkyl or aryl$(C_{1-6})$alkyl;

$R^{30}$ represents, independently, each time that it occurs, $(C_{1-6})$alkyl, —O—$R^8$, —S(O)$_{n6}R^8$, —S(O)$_{n7}$N($R^8R^9$), —N($R^8R^9$), —CN, —NO$_2$, —CO$_2R^8$, —CON($R^8R^9$), —NCO—$R^8$, or halogen, each of n6 and n7 representing, independently, each time that it occurs, 0, 1 or 2;

said heterocyclyl radical being azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulphone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl-N-oxide, quinoxalinyl, tetrahydrofuryl, tetrahydroisoquinolinyl, tetrahydro-quinolinyl, thiamorpholinyl, thiamorpholinyl sulphoxide, thiazolyl, thiazolinyl, thienofuryl, thienothienyl or thienyl;

said aryl radical being phenyl or naphthyl;

it being understood that:

when n1=1, $R^{10}$ is C and $R^6$ represents H, then $R^{10}$ and $R^7$ can, taken together, form the

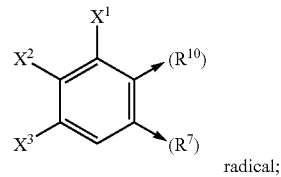
radical;

or when n1=1, $R^{10}$ is C, and $R^7$ is =O, —H, or =S, then $R^{10}$ and $R^6$ can, taken together, form the

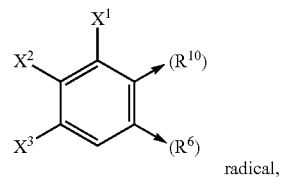
radical, with each of $X^1$, $X^2$, and $X^3$ representing, independently, H, a halogen atom, —NO$_2$, —NCO—$R^8$, —CO$_2R^8$, —CN, or —CON($R^8R^9$); and when $R^1$ is N($R^{24}R^{25}$), then n3 represents 1, each of n4 and n5 represents 0, Z is a bond, and $R^3$ and $R^{11}$ can, taken together, form the

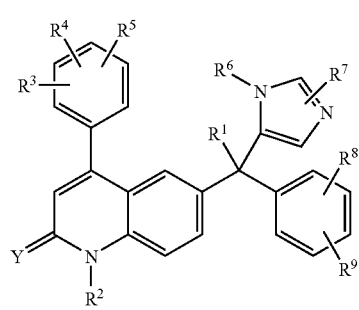
radical, with n2 representing an integer from 1 to 6, and each of $X^4$ and $X^5$ representing, independently, H, $(C_{1-6})$alkyl or aryl, or $X^4$ and $X^5$ taken together, forming a $(C_{3-6})$cycloalkyl radical;

of a compound of general formula (III)

(III)

in which:

$R^1$ represents H or an alkyl, $OR^{10}$, $SR^{10}$ or $NR^{11}R^{12}$ radical;

$R^2$ represents H or an alkyl radical;

$R^3$, $R^4$ and $R^5$ represent, independently, H, a halogen atom or an alkyl, trihalomethyl, hydroxy, cyano or alkoxy radical;

$R^6$ represents H or an alkyl radical;

$R^7$ represents H, a halogen atom or an alkyl, hydroxyalkyl, amino, hydroxycarbonyl radical;

$R^8$ and $R^9$ represent, independently, H, a halogen atom or a cyano, alkyl, trihalomethyl, alkoxy, alkylthio or dialkylamino radical;

$R^{10}$ represents H or an alkyl or alkylcarbonyl radical;

$R^{11}$ represents H or an alkyl radical;

$R^{12}$ represents H or an alkyl or alkylcarbonyl radical;

and Y represents O or S;

and a pharmaceutically acceptable salt of a compound of general formula (II) or of a compound of general formula (III).

In certain cases, compounds which are of use in the composition of a product according to the present invention can comprise asymmetrical carbon atoms. As a result, said compounds have two possible enantiomeric forms, i.e. the "R" and "S" configurations. The present invention includes the two enantiomeric forms and all combinations of these forms, including the racemic mixtures "RS". In an effort to simplify matters, when no specific configuration is as indicated in the structural formulae, it should be understood that both enantiomeric forms and their mixtures are represented.

By alkyl, unless specified otherwise, is meant a linear or branched alkyl radical containing 1 to 6 carbon atoms. By alkylcarbonyl, alkylthio, alkoxy, alkylamino, dialkylamino, alkenyl, alkynyl, aralkyl, heterocyclylalkyl radicals, is meant respectively the alkylcarbonyl, alkylthio, alkoxy, alkylamino, dialkylamino, alkenyl, alkynyl, aralkyl, heterocyclylalkyl radicals of which the alkyl radical has the meaning indicated previously.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. Finally, by halogen, is meant the fluorine, chlorine, bromine or iodine atoms.

When a chemical structure such as used here has an arrow emanating from it, the arrow indicates the attachment point. For example, the structure

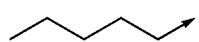

is a pentyl radical. When a value in brackets appears close to the arrow, the value indicates where the attachment point can be found in the compound. For example, in general formula (II)

(II)

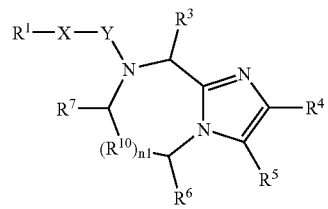

as defined previously, when $R^{10}$ and $R^7$ are taken together to form the

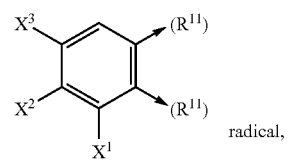

radical, the following structure results:

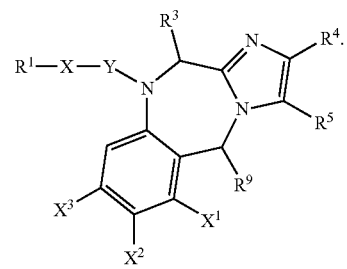

Finally, by pharmaceutically acceptable salt, is meant in particular the addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. The salts formed from bases such as sodium or potassium hydroxide also fall within the scope of the present invention, when they can be used. For other examples of pharmaceutically acceptable salts, reference can be made to "Salt selection for basic drugs", *Int. J. Pharm.* (1986), 33, 201–217.

In particular, transduction inhibitors of heterotrimeric G protein signals could, according to the invention, be usefully combined with the following compounds:

Prenyltransferase inhibitors, and in particular farnesyltransferase inhibitors such as 1-(2-(1-((4-cyano)phenylmethyl)imidazol-4-yl)-1-oxoethyl-2,5-dihydro-4-(2-methoxyphenyl)imidazo[1,2c][1,4]benzodiazepine, 4-(2-bromophenyl)-1-(2-(1-((4-cyano-3-methoxy) phenylmethyl)-imidazol-5-yl)-1-oxoethyl)-1,2-dihydro-8-fluoro-imidazo[1,2a][1,4]-benzodiazepine or (±)-4-(3-chlorophenyl)-6-[(4-chlorophenyl)-amino-(1-methyl-1H-imidazol-5-yl)methyl]-1-methyl-2(1H)quinolinone;

cell spindle poisons such as taxol;

alkylating agents such as cisplatin;

anti-metabolic agents such as gemcitabine or 5-fluorouracyl.

Preferably, the transduction inhibitors of heterotrimeric G protein signals used in the invention are such that they correspond to general sub-formula ($I_A$) as defined previously in which:

$R_1$ represents H;

$R_2$ and $R_3$ represent, independently, H or a lower alkyl radical;

$R_4$ represents O;

$R_5$ represents H, or one of the lower alkyl, cycloalkyl or cycloalkylalkyl radicals;

$R_6$ represents an aryl radical optionally substituted by radicals chosen from the group comprising the OH, alkyl or lower alkoxy, $N(R_{10})(R_{11})$, COOH, $CON(R_{10})(R_{11})$ and halo radicals;

$R_{10}$ and $R_{11}$, representing independently H or a lower alkyl radical;

or are salts of these same compounds.

Preferably, when they are used for the invention, the compounds of general formula (II) are those in which are found, independently, the radicals presenting the following characteristics:

$R^1$ representing the

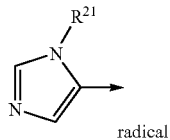

radical $R^{21}$ representing an aralkyl radical the aryl group of which can be optionally substituted by a radical or radicals chosen from a halogen atom and the cyano, hydroxy, alkoxy, amino, alkylamino and dialkylamino radicals;

$R^4$ representing an aryl radical optionally substituted by a radical or radicals chosen from a halogen atom and the hydroxy, alkoxy, amino, alkylamino and dialkylamino radicals;

X representing an alkylene radical containing 1 to 6 carbon atoms;

Y representing CO;

n1=1, $R^{10}$ being C, $R^6$ representing H and $R^{10}$ and $R^7$ taken together, forming the

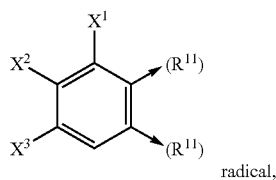

radical, each of $X^1$, $X^2$, and $X^3$ representing, independently, H or a halogen atom.

Preferably, when they are used for the invention, the compounds of general formula (III) are those in which are found, independently, the radicals presenting the following characteristics:

$R^1$ representing OH or $NH_2$;

$R^2$ representing alkyl and preferably methyl;

one of $R^3$, $R^4$ and $R^5$ representing a halogen atom;

$R^6$ representing alkyl and preferably methyl;

one of $R^8$ and $R^9$ representing a halogen atom;

Y representing O.

According to a particularly preferred variant of the invention, the transduction inhibitors of heterotrimeric G protein signals are chosen from the group composed of:

7-(2-amino-1-oxo-3-thiopropyl)-8-(cyclohexylmethyl)-2-(2-methylphenyl)-5,6,7,8-tetrahydroimidazo[1,2a]pyrazine; and 7-(2-amino-1-oxo-3-thiopropyl)-8-(cyclohexylmethyl)-2-phenyl-5,6,7,8-tetrahydroimidazo[1,2a]pyrazine;

and pharmaceutically acceptable salts of the latter.

Still according to a particularly preferred variant of the invention, the anti-cancer agents combined with said transduction inhibitors of heterotrimeric G protein signals are chosen from the group composed of:

1-(2-(1-((4-cyano)phenylmethyl)imidazol-4-yl)-1-oxoethyl-2,5-dihydro-4-(2-methoxyphenyl)imidazo[1,2c][1,4]benzodiazepine;

4-(2-bromophenyl)-1-(2-(1-((4-cyano-3-methoxy)phenylmethyl)-imidazo-5-yl)-1-oxoethyl)-1,2-dihydro-8-fluoro-imidazo[1,2a][1,4]-benzodiazepine;

(±)-4-(3-chlorophenyl)-6-[(4-chlorophenyl)-amino-(1-methyl-1H-imidazol-5-yl) methyl]-1-methyl-2(1H)quinolinone;

taxol;

gemcitabine;

and of the pharmaceutically acceptable salts of the latter.

Optionally, an additional anti-cancer compound can also be used, different from the anti-cancer agent combined with the transduction inhibitor of heterotrimeric G protein signals, in the composition of the product of the invention. Preferably, said additional compound is chosen from the group composed:

1-(2-(1-((4-cyano)phenylmethyl)imidazol-4-yl)-1-oxoethyl-2,5-dihydro-4-(2-methoxyphenyl)imidazo[1,2c][1,4]benzodiazepine;

4-(2-bromophenyl)-1-(2-(1-((4-cyano-3-methoxy)phenylmethyl)-imidazo-5-yl)-1-oxoethyl)-1,2-dihydro-8-fluoro-imidazo[1,2a][1,4]-benzodiazepine (±)-4-(3-chlorophenyl)-6-[(4-chlorophenyl)-amino-(1-methyl-1H-imidazol-5-yl)methyl]-1-methyl-2(1H)quinolinone;

taxol;

gemcitabine;

and pharmaceutically acceptable salts of the latter.

A subject of the invention is also a pharmaceutical composition comprising at least one of the products according to the invention.

The pharmaceutical compositions comprising a product according to the invention can be in the form of a solid, for example powders, granules, tablets, gelatin capsules, liposomes or suppositories. The appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions comprising a product according to the invention can also be presented in liquid form, for example, solutions, emulsions, suspensions or syrups. The appropriate liquid supports can, for example, be water, organic solvents such as glycerol or glycols, and similarly their mixtures, in varying proportions, in water.

The administration of a medicament according to the invention can be done by topical, oral, parenteral route, by injection (intramuscular, sub-cutaneous, intravenous, etc.), etc. The administration route will depend of course on the type of disease to be treated.

The following administration doses (daily, except for contra-indication) could be envisaged for the different compounds used in the composition of a product according to the invention:

compound of general formula (I): from 50 to 200 mg/m$^2$ by intraperitoneal route;

compound of general formula (II): from 50 to 500 mg/m$^2$ per os;

taxol: 1 to 10 mg/kg (intraperitoneal route) or 1 to 3 mg/kg (intravenous route);

cisplatin: 50 to 80 mg/M$^2$;

5-fluorouracil: 400 to 800 mg/M$^2$ by intravenous route, the administrations being repeated from 1 to 4 times per month;

gemcitabine: 100 to 500 mg/M$^2$ by intravenous route (perfusions lasting approximately 6 hours).

Preparation of Certain Compounds Used in the Composition of the Products of the Invention:

I) The compounds of general formula (I) are prepared according to methods similar to those described in PCT Patent Application WO 97/30053.

However, the following compounds have been described previously in Patent Application WO 00/02881:

7-(2-amino-1-oxo-3-thiopropyl)-8-(cyclohexylmethyl)-2-(2-methylphenyl)-5,6,7,8-tetrahydroimidazo[1,2a]pyrazine; and 7-(2-amino-1-oxo-3-thiopropyl)-8-(cyclohexylmethyl)-2-phenyl-5,6,7,8-tetrahydroimidazo[1,2a]pyrazine.

II) The compounds of general formula (II), of which 1-(2-(1-((4-cyano)phenylmethyl)imidazol-4-yl)-1-oxoethyl-2,5-dihydro-4-(2-methoxyphenyl) imidazo[1,2c][1,4]benzodiazepine and 4-(2-bromophenyl)-1-(2-(1-((4-cyano-3-methoxy)phenylmethyl)imidazo-5-yl)-1-oxoethyl)-1,2-dihydro-8-fluoroimidazol [1,2a][1,4]-benzodiazepine, are prepared according to the procedures described in PCT Patent Application WO 00/39130.

C) The compounds of general formula (III) are prepared according to the methods described in PCT Patent Application WO 97/21701.

Unless they are defined differently, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no event be considered as a limit to the scope of the invention.

EXAMPLES

In order to illustrate the usefulness of the invention, the effect of a treatment on a tumor line of Mia-Paca2 pancreatic human cells with 7-(2-amino-1-oxo-3-thiopropyl)-8-(cyclohexylmethyl)-2-(2-methylphenyl)-5,6,7,8-tetrahydroimidazo[1,2a]pyrazine or 7-(2-amino-1-oxo-3-thiopropyl)-8-(cyclohexylmethyl)-2-phenyl-5,6,7,8-tetrahydroimidazo[1,2a]pyrazine (described in PCT Application WO 00/02881) combined with different anti-cancer agents will be studied.

By convention, the products inhibiting the transduction of heterotrimeric G protein signals used in the tests are identified by the letter A, and the other anti-cancer agents used in the tests by the letter B.

1) Procedures

Material

The following compounds (prepared according to the methods described previously) are of use in the composition of the products tested:

7-(2-amino-1-oxo-3-thiopropyl)-8-(cyclohexylmethyl)-2-(2-methylphenyl)-5,6,7,8-tetrahydroimidazo[1,2a]pyrazine (compound $A_1$);

7-(2-amino-1-oxo-3-thiopropyl)-8-(cyclohexylmethyl)-2-phenyl-5,6,7,8-tetrahydroimidazo[1,2a]pyrazine (compound $A_2$);

1-(2-(1-((4-cyano)phenylmethyl)imidazol-4-yl)-1-oxoethyl-2,5-dihydro-4-(2-methoxyphenyl)imidazo[1,2c][1,4]benzodiazepine (compound $B_1$);

taxol (compound $B_2$);

gemcitabine (compound $B_3$);

(±)-4-(3-chlorophenyl)-6-[(4-chlorophenyl)-amino-(1-methyl-1H-imidazol-5-yl)methyl]-1-methyl-2(1H)quinolinone (compound $B_4$);

4-(2-bromophenyl)-1-(2-(1-((4-cyano-3-methoxy)phenylmethyl)-imidazo-5-yl)-1-oxoethyl)-1,2-dihydro-8-fluoroimidazo[1,2a][1,4]-benzodiazepine (compound $B_5$).

Cell Line

The cell line Mia-Paca2 (human pancreatic cancer cells) was acquired from the American Tissue Culture Collection (Rockville, Md., USA).

Measurement of Cell Proliferation In Vitro

The Mia-Paca2 cells (1500 cells/wells) are cultured in 96-well plates pre-coated with polyhema (Sigma) which allows only the growth of cells presenting a tumorigenic phenotype.

On day 0, these cells are seeded in 90 μl of Dulbecco's modified Eagle medium (Gibco-Brl, Cergy-Pontoise, France) completed with 10% of foetal calf serum inactivated by heating (Gibco-Brl, Cergy-Pontoise, France), 50000 units/l of penicillin and 50 mg/l streptomycin (Gibco-Brl, Cergy-Pontoise, France), and 2 mM of glutamin (Gibco-Brl, Cergy-Pontoise, France).

The cells were treated with increasing concentrations of two products alone or combined in a matrix, i.e.: on day 1, with the first product for 96 hours and on day 2 with the second product for 72 hours. According to method α, the transduction inhibitor of heterotrimeric G protein signals with which the anti-cancer agent is combined is administered before the latter, then according to method β, it is done so after.

At the end of this period, quantification of cell proliferation is evaluated by a colorimetric test based on the cleavage of the tetrazolium salt WST1 by mitochondrial dehydrogenases in the living cells leading to the formation of formazan (Boehringer Mannheim, Meylan, France). These tests are carried out in duplicate with 4 measurements for each single product and for each combination tested. This allows the number of living cells at the end of each treatment to be determined, i.e. the observed value. The calculated value of the living cells for each treatment corresponds to the multiplication of the observed values of the effects of separate products. These observed and calculated values are compared for each combination. When the observed value of living cells is lower than the calculated value of the living cells, a synergy is considered to exist. When the observed value is equal to the calculated value, a additive effect is considered to exist. When the observed value is greater than the calculated value, an antagonism is considered to exist.

2) Results:

The results obtained are given in the tables shown below.

The results given in Tables I, II, I, IV and IV show that the products comprising compound $A_1$ combined with compound $B_1$, compound $B_2$ or compound $B_3$ or those comprising compound $A_2$ combined with compound $B_4$ or compound $B_5$ are capable of inhibiting the proliferation in vitro of Mia-Paca2 human tumor cells. The combined effect of the combination, evaluated by the method described in Cote, S. and Momparler, R. L., *Anticancer Drugs* (1993), 4, 327–333, allows a synergy in combinations $A_1+B_1$, $A_1+B_2$, $A_1+B_3$, $A_2+B_4$ and $A_2+B_5$ to be noted.

TABLE I

| Doses of compound $B_1$ | Compound $B_1$ alone | Observed values (method $\alpha$ – n = 4) Compound $A_1$ (20 μM) + compound $B_1$ | Calculated values Compound $A_1$ (20 μM) + compound $B_1$ |
|---|---|---|---|
| 0 μM | 100 | 51 ± 8.9 | |
| 0.04 μM | 94 ± 2.3 | 39 ± 8.4 | 47 ± 7.1 |
| 0.2 μM | 80 ± 4.2 | 23 ± 5.9 | 38 ± 4.9 |
| 1 μM | 68 ± 2.3 | 23 ± 6.5 | 34 ± 5.0 |

TABLE II

| Doses of compound $B_2$ | Compound $B_2$ alone | Observed values (method $\alpha$ – n = 3) Compound $A_1$ (20 μM) + compound $B_2$ | Calculated values Compound $A_1$ (20 μM) + compound $B_2$ |
|---|---|---|---|
| 0 nM | 100 | 49 ± 7.7 | |
| 0.8 nM | 100 ± 5.8 | 34 ± 2.4 | 48 ± 6.7 |
| 4 nM | 100 ± 0.3 | 32 ± 2.2 | 49 ± 7.5 |
| 20 nM | 60 ± 10.6 | 17 ± 4.5 | 30 ± 7.2 |

TABLE III

| Doses of compound $B_3$ | Compound $B_3$ alone | Observed values (method $\alpha$ – n = 3) Compound $A_1$ (20 μM) + compound $B_3$ | Calculated values Compound $A_1$ (20 μM) + compound $B_3$ |
|---|---|---|---|
| 0 nM | 100 | 65 ± 7.3 | |
| 4 nM | 95 ± 9.8 | 48 ± 2.1 | 59 ± 1.3 |
| 20 nM | 72 ± 11.5 | 27 ± 6.8 | 45 ± 4.0 |
| 100 nM | 62 ± 1.9 | 30 ± 4.0 | 40 ± 3.1 |

TABLE IV

| Doses of compound $B_4$ | Compound $B_4$ alone | Observed values (method $\beta$ – n = 2) Compound $A_2$ (20 μM) + compound $B_4$ | Calculated values Compound $A_2$ (20 μM) + compound $B_4$ |
|---|---|---|---|
| 0 nM | 100 | 42 ± 11.0 | |
| 40 nM | 104 ± 2.0 | 28 ± 3.0 | 44 ± 12.0 |
| 0.2 μM | 90 ± 9.0 | 13 ± 2.0 | 37 ± 6.0 |
| 1 μM | 72 ± 3 | 14 ± 1.0 | 30 ± 7.0 |

TABLE V

| Doses of compound $B_5$ | Compound $B_5$ alone | Observed values (method $\beta$ – n = 3) Compound $A_2$ (20 μM) + compound $B_5$ | Calculated values Compound $A_2$ (20 μM) + compound $B_5$ |
|---|---|---|---|
| 0 μM | 100 | 44 ± 6.4 | |
| 0.2 μM | 86 ± 0.9 | 17 ± 2.7 | 38 ± 5.2 |
| 1 μM | 63 ± 2.6 | 11 ± 1.4 | 27 ± 3.0 |

What is claimed is:

1. A composition comprising a therapeutically effective amount of a) -7-(2-amino-1-oxo-3-thiopropyl)-8-(cyclohexylmethyl)-2-phenyl)-5,6,7,8-tetrahydroimidazo[1,2a]pyrazine; or its dimeric form or its non-toxic, pharmaceutically acceptable acid addition salts and b) cisplatin.

2. A composition of claims 1 comprising 7-(2-amino-1-oxo-3-thiopropyl)-8-(cyclohexylmethyl)-2-phenyl)-5,6,7,8-tetrahydroimidazo[1,2a]pyrazine; or its non-toxic, pharmaceutically acceptable acid addition salts and cisplatin.

* * * * *